(12) United States Patent
Hossainy et al.

(10) Patent No.: US 6,764,505 B1
(45) Date of Patent: Jul. 20, 2004

(54) VARIABLE SURFACE AREA STENT

(75) Inventors: Syed Hossainy, Fremont, CA (US);
Fuh-Wei Tang, Temecula, CA (US);
Brian P. Cahill, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 132 days.

(21) Appl. No.: 09/834,012

(22) Filed: Apr. 12, 2001

(51) Int. Cl.$^7$ .................................................. A61F 2/08
(52) U.S. Cl. .................... 623/1.15; 427/2.25; 623/1.39
(58) Field of Search ............................ 623/1.15, 1.42, 623/1.39; 427/2.25

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,931,287 A | 6/1990 | Bae et al. | 424/484 |
| 4,977,901 A | 12/1990 | Ofstead | 128/772 |
| 4,994,560 A | 2/1991 | Kruper, Jr. et al. | |
| 5,040,548 A | 8/1991 | Yock | 128/898 |
| 5,059,166 A | 10/1991 | Fischell | 600/3 |
| 5,064,435 A | 11/1991 | Porter | 623/12 |
| 5,087,244 A | 2/1992 | Wolinsky | 604/53 |
| 5,100,429 A | 3/1992 | Sinofsky et al. | |
| 5,213,561 A | 5/1993 | Weinstein et al. | |
| 5,229,172 A | 7/1993 | Cahalan et al. | |
| 5,232,444 A | 8/1993 | Just | 604/96 |
| 5,258,419 A | 11/1993 | Rolando et al. | |
| 5,278,200 A | 1/1994 | Coury et al. | |
| 5,308,641 A | 5/1994 | Cahalan et al. | |
| 5,328,471 A | 7/1994 | Slepian | 604/101 |
| 5,336,518 A | 8/1994 | Narayanan et al. | |
| 5,342,283 A | 8/1994 | Good | |
| 5,342,621 A | 8/1994 | Eury | 424/423 |
| 5,344,455 A | 9/1994 | Keogh et al. | |
| 5,350,800 A | 9/1994 | Verhoeven et al. | |

(List continued on next page.)

FOREIGN PATENT DOCUMENTS

| | | |
|---|---|---|
| DE | 19916086 | 10/1999 |
| EP | 0 627 226 | 12/1994 |
| EP | 0665023 | 8/1995 |
| EP | 0701803 | 3/1996 |
| EP | 0850604 | 7/1998 |

(List continued on next page.)

OTHER PUBLICATIONS

U.S. patent application Ser. No. 09/833,908, Hossainy et al.
U.S. patent application Ser. No. 09/833,946, Hossainy et al.
U.S. patent application Ser. No. 09/390,855, Hossainy et al.
U.S. patent application Ser. No. 09/390,069, Hossainy et al.
Liermann, Dieter et al., "Prophylactic Endovascular Radiotherapy to Prevent Intimal Hyperplasia after Stent Implantation in Femoropopliteal Arteries", *CardioVascular and Interventional Radiology* 17:12–16, 1994; Springer–Veriag, New York, Inc.

(List continued on next page.)

*Primary Examiner*—David J. Isabella
*Assistant Examiner*—Thomas Sweet
(74) *Attorney, Agent, or Firm*—Squire, Sanders & Dempsey, L.L.P.

(57) ABSTRACT

A stent of variable surface area as determined by stent struts. The stent can have a variable surface area per unit length which accommodates a therapeutic agent. A patterned distribution of therapeutic agent can be provided throughout the stent. The stent can have an increased level of therapeutic agent near an end of the stent. A decreased level of therapeutic agent can be provided near an end of one embodiment of a stent. Indentations can be provided at the surface of the stent with therapeutic agent disposed therein. The stent can be cut with struts of variable thickness to provide the variable stent surface area.

29 Claims, 4 Drawing Sheets

U.S. PATENT DOCUMENTS

| | | |
|---|---|---|
| 5,366,504 A | 11/1994 | Anderson et al. |
| 5,411,466 A | 5/1995 | Hess |
| 5,415,938 A | 5/1995 | Cahalan et al. |
| 5,429,618 A | 7/1995 | Keogh |
| 5,443,496 A | 8/1995 | Schwartz et al. ............... 623/1 |
| 5,464,450 A | 11/1995 | Buscemi et al. |
| 5,464,650 A | 11/1995 | Berg et al. .................... 427/2.3 |
| 5,470,313 A | 11/1995 | Crocker ........................ 604/96 |
| 5,476,509 A | 12/1995 | Keogh et al. |
| 5,500,013 A | 3/1996 | Buscemi et al. |
| 5,551,954 A | 9/1996 | Buscemi et al. |
| 5,554,182 A | 9/1996 | Dinh et al. |
| 5,571,166 A | 11/1996 | Dinh et al. |
| 5,578,073 A | 11/1996 | Haimovich et al. ............. 623/1 |
| 5,591,224 A | 1/1997 | Schwartz et al. |
| 5,591,227 A | 1/1997 | Dinh et al. |
| 5,599,352 A | 2/1997 | Dinh et al. |
| 5,605,696 A | 2/1997 | Eury et al. .................. 424/423 |
| 5,624,411 A | 4/1997 | Tuch .......................... 604/265 |
| 5,628,730 A | 5/1997 | Shapland et al. ............. 604/21 |
| 5,628,785 A | 5/1997 | Schwartz et al. |
| 5,637,113 A | 6/1997 | Tartaglia et al. ............... 623/1 |
| 5,649,951 A | 7/1997 | Davidson ................... 606/198 |
| 5,649,977 A | 7/1997 | Campbell ...................... 623/1 |
| 5,667,767 A | 9/1997 | Greff et al. ............. 424/9.411 |
| 5,670,558 A | 9/1997 | Onishi et al. ................ 523/112 |
| 5,674,242 A | 10/1997 | Phan et al. ................. 606/198 |
| 5,693,085 A | 12/1997 | Buirge et al. |
| 5,693,376 A | 12/1997 | Fetherston et al. |
| 5,697,967 A | 12/1997 | Dinh et al. |
| 5,700,286 A | 12/1997 | Tartaglia et al. |
| 5,702,818 A | 12/1997 | Cahalan et al. |
| 5,707,385 A | 1/1998 | Williams .................... 606/192 |
| 5,711,812 A | 1/1998 | Chapek et al. |
| 5,713,949 A | 2/1998 | Jayaraman |
| 5,716,981 A | 2/1998 | Hunter et al. ............... 514/449 |
| 5,722,984 A | 3/1998 | Fischell et al. |
| 5,730,698 A | 3/1998 | Fischell et al. |
| 5,766,710 A | 6/1998 | Turnlund et al. |
| 5,769,883 A | 6/1998 | Buscemi et al. |
| 5,769,884 A * | 6/1998 | Solovay ..................... 623/1.13 |
| 5,782,742 A | 7/1998 | Crocker et al. ................ 600/3 |
| 5,800,392 A | 9/1998 | Racchini ...................... 604/96 |
| 5,811,151 A | 9/1998 | Hendriks et al. |
| 5,824,048 A | 10/1998 | Tuch .............................. 623/1 |
| 5,824,049 A | 10/1998 | Ragheb et al. ................. 623/1 |
| 5,826,586 A | 10/1998 | Mishra et al. ............... 128/898 |
| 5,830,178 A | 11/1998 | Jones et al. ................... 604/49 |
| 5,837,313 A | 11/1998 | Ding et al. |
| 5,840,009 A | 11/1998 | Fischell et al. |
| 5,843,172 A | 12/1998 | Yan |
| 5,851,508 A | 12/1998 | Greff et al. ............. 424/9.411 |
| 5,857,998 A | 1/1999 | Barry |
| 5,858,556 A | 1/1999 | Eckert et al. ............... 428/586 |
| 5,858,990 A | 1/1999 | Walsh ......................... 514/44 |
| 5,865,814 A | 2/1999 | Tuch .......................... 604/265 |
| 5,866,113 A | 2/1999 | Hendriks et al. |
| 5,871,436 A | 2/1999 | Eury |
| 5,871,437 A | 2/1999 | Alt |
| 5,873,904 A | 2/1999 | Ragheb et al. |
| 5,893,840 A | 4/1999 | Hull et al. |
| 5,897,911 A | 4/1999 | Loeffler ..................... 427/2.25 |
| 5,898,178 A | 4/1999 | Bunker ...................... 250/423 |
| 5,902,631 A | 5/1999 | Wang et al. ................. 427/2.1 |
| 5,916,234 A | 6/1999 | Lam |
| 5,925,552 A | 7/1999 | Keogh et al. |
| 5,928,916 A | 7/1999 | Keogh |
| 5,951,881 A | 9/1999 | Rogers et al. ................ 216/41 |
| 5,968,091 A | 10/1999 | Pinchuk et al. ................ 623/1 |
| 5,968,092 A | 10/1999 | Buscemi et al. |
| 5,971,954 A | 10/1999 | Conway et al. ............... 604/96 |
| 5,972,027 A | 10/1999 | Johnson |
| 5,972,029 A | 10/1999 | Fuisz ............................. 623/1 |
| 5,980,564 A | 11/1999 | Stinson ......................... 623/1 |
| 5,980,928 A | 11/1999 | Terry .......................... 424/427 |
| 5,980,972 A | 11/1999 | Ding ......................... 427/2.24 |
| 5,997,517 A | 12/1999 | Whitbourne ............... 604/265 |
| 6,010,530 A | 1/2000 | Goicoechea ................... 623/1 |
| 6,013,099 A | 1/2000 | Dinh et al. ..................... 623/1 |
| 6,015,541 A | 1/2000 | Greff et al. ................ 424/1.25 |
| 6,019,789 A | 2/2000 | Dinh et al. ..................... 623/1 |
| 6,024,918 A | 2/2000 | Hendriks et al. |
| 6,027,526 A * | 2/2000 | Limon et al. ............. 623/1.15 |
| 6,033,719 A | 3/2000 | Keogh |
| 6,042,606 A * | 3/2000 | Frantzen .................... 623/1.18 |
| 6,042,875 A | 3/2000 | Ding et al. ................. 427/2.24 |
| 6,059,752 A | 5/2000 | Segal ......................... 604/107 |
| 6,071,305 A | 6/2000 | Brown et al. |
| 6,080,099 A | 6/2000 | Slater et al. ................... 600/8 |
| 6,080,190 A | 6/2000 | Schwartz |
| 6,093,199 A | 7/2000 | Brown et al. |
| 6,096,070 A | 8/2000 | Ragheb et al. ................. 623/1 |
| 6,099,455 A | 8/2000 | Columbo et al. |
| 6,099,559 A | 8/2000 | Nolting ..................... 623/1.16 |
| 6,099,561 A | 8/2000 | Alt ............................ 623/1.44 |
| 6,106,454 A | 8/2000 | Berg et al. ..................... 600/3 |
| 6,110,483 A | 8/2000 | Whitbourne et al. ........ 424/423 |
| 6,140,127 A | 10/2000 | Sprague ...................... 435/395 |
| 6,140,431 A | 10/2000 | Kinker et al. ................. 526/79 |
| 6,149,574 A | 11/2000 | Trauthen et al. ............... 600/3 |
| 6,153,252 A | 11/2000 | Hossainy et al. ............ 427/2.3 |
| 6,165,212 A | 12/2000 | Dereume et al. .......... 623/1.13 |
| 6,168,619 B1 | 1/2001 | Dinh et al. ................. 623/1.13 |
| 6,203,551 B1 | 3/2001 | Wu ............................ 606/108 |
| 6,214,901 B1 | 4/2001 | Chudzik et al. ............. 523/113 |
| 6,224,894 B1 | 5/2001 | Jamiolkowski et al. ..... 424/426 |
| 6,231,590 B1 | 5/2001 | Slaikeu et al. .............. 606/200 |
| 6,242,041 B1 | 6/2001 | Katoot et al. .............. 427/2.24 |
| 6,253,443 B1 * | 7/2001 | Johnson ....................... 29/557 |
| 6,254,632 B1 * | 7/2001 | Wu et al. .................. 623/1.15 |
| 6,258,121 B1 | 7/2001 | Yang et al. ................ 623/1.46 |
| 6,262,034 B1 | 7/2001 | Mathiowitz et al. .......... 514/44 |
| 6,273,850 B1 | 8/2001 | Gambale ....................... 600/3 |
| 6,273,913 B1 * | 8/2001 | Wright et al. ............. 623/1.42 |
| 6,287,628 B1 | 9/2001 | Hossainy et al. ............ 427/2.3 |
| 6,296,603 B1 | 10/2001 | Turnlund et al. .............. 600/3 |
| 6,319,520 B1 | 11/2001 | Wuthrich et al. ............ 424/482 |
| 6,344,035 B1 | 2/2002 | Chudzik et al. ............. 604/265 |
| 6,379,379 B1 | 4/2002 | Wang ........................ 623/1.15 |
| 6,379,381 B1 * | 4/2002 | Hossainy et al. .......... 623/1.42 |
| 6,413,272 B1 * | 7/2002 | Igaki .......................... 623/1.15 |
| 6,488,701 B1 * | 12/2002 | Nolting et al. ............. 623/1.13 |
| 6,504,307 B1 | 1/2003 | Malik et al. ............. 315/111.21 |
| 6,524,232 B1 | 2/2003 | Tang et al. ..................... 600/3 |
| 6,554,758 B2 | 4/2003 | Turnlund et al. .............. 600/3 |
| 6,582,417 B1 | 6/2003 | Ledesma et al. ............ 604/529 |
| 6,605,114 B1 * | 8/2003 | Yan et al. .................. 623/1.43 |

FOREIGN PATENT DOCUMENTS

| | | |
|---|---|---|
| EP | 0 850 651 | 7/1998 |
| EP | 0970711 | 1/2000 |
| EP | 0972498 | 1/2000 |
| EP | 1103234 | 5/2001 |
| WO | WO 90/01969 | 3/1990 |
| WO | WO91/12846 | 9/1991 |
| WO | WO97/45105 | 12/1997 |
| WO | WO 98/23228 | 6/1998 |
| WO | WO99/63981 | 12/1999 |
| WO | WO00/12147 | 3/2000 |
| WO | WO00/64506 | 11/2000 |
| WO | WO01/01890 | 1/2001 |

| WO | WO 01/45763 | 6/2001 |
| WO | WP 01/91918 | 12/2001 |
| WO | WO 02/47731 | 6/2002 |

OTHER PUBLICATIONS

Fischell, Robert E. et al., "The Radioisotope Stent: Conception and Implementation", Discoveries in Radiation for Restenosis, Abstract 37, p115, Jan. 1996.

Tierstein, Paul S. et al., Catheter–Based Radiation Therapy to Inhibit Restenosis Following Coronary Stenting, Discoveries in Radiation for Restenosis, Abstract 31, p99, Jan. 1996.

Louis G. Martin, "Radiation for Peripheral Applications: Technical Aspects", Discoveries in Radiation for Restenosis, Abstract 27, p81–82, Jan. 1996.

Li, Alexander N. et al., "A Novel Brachyehtapy Source for Treatment of Coronary Artery Restenosis", Discoveries in Radiation for Restenosis, Abstract 24, pp67–72, Jan. 1996.

Hehrlein, C. and Fehsenfeld, P., "Radioactive Stents", Discoveries in Radiation for Restenosis, Abstract 22, p63–64, Jan. 1996.

Hehrlein, Christoph et al., "Low–Dose Radioactive Endovascular Stents Prevent Smooth Muscle Cell Proliferation and Newointimal Hyperplasia in Rabbits", *Circulation*, vol. 92(6):1570–1575, Sep. 15, 1995.

Fischell, Tim A. et al., "Low–Dose, β–Particle Emission from 'Stent' Wire Results in Complete, Localized Inhibition of Smooth Muscle Cell Proliferation", *Circulation*, vol. 90(6):2956–2963, Dec. 1994.

Scheuer, J.T., et al., "Model of Plasma Source Ion Implantation in Planar, Cylindrical, and Spherical Geometries", J. Appl. Phys 67 (3), Feb. 1, 1990, 1990 American Institute of Physics.

Malik, Sharmin M., et al., Development of An Energetic Ion Assisted Mixing and Deposition Process for $TIN_x$ and Diamondlike Carbon Films, Using a Co–axial Geometry in Plasma Source Ion Implantation, J. Vac Sci. Technol. A 15(6), Nov./Dec. 1997, 1997 American Vacuum Society.

Wiesendanger, R., et al., "Microelectronics and Nanometer Structures", Journal of Vaccuum Science & Technology B, Second Series vol. 12, Mar./Apr. 1994.

Malik, Shamim M., et al., "Overview of Plasma Source Ion Implantation Research at University of Wisconsin–Madison", J. Vac. Sci. Technol. B 12(2), Mar./Apr. 1994, 1994 American Vacuum Society.

Shamim, M., et al, "Measurements of Spatial and Temporal Sheath Evolution for Spherical and Cylindrical Geometrics In Plasma Source Ion Implantation", J. Appl Phys. 69(5), Mar. 1, 1991, 1991 American Institute of Physics.

Shamim, M. M., et al., "Measurements of Electron Emission Due to Energetic Ion Bombardment in Plasma Source Ion Implantation", J. Appl. Phys. 70(9), Nov. 1, 1991, 1991 American Institute of Physics.

Malik, Shamim M., "Sheath Dynamics and Dose Analysis for Planar Targets in Plasma Source Ion Implantation", Plasma Sources Sci Technol. 2 (1993) 81–85. Printed in UK.

Lieberman, Michael A., et al., "Principles Of Plasma Discharges And Materials Processing", A Wiley–Interscience Publication, John Wiley & Sons, Inc., 1994.

U.S. patent application Ser. No. 09/697,103, Hossainy et al., filed Oct. 26, 2000.

* cited by examiner

VARIABLE SURFACE AREA STENT

BACKGROUND OF THE INVENTION

The present invention relates to intravascular implants. In particular, the present invention relates to stent devices to deliver therapeutic agents such as radioisotopes or drugs.

BACKGROUND OF THE PRIOR ART

In the last several years, minimally invasive surgical procedures have become increasingly common. Minimally invasive procedures such as percutaneous transluminal coronary angioplasty (PTCA) are widely utilized. A PTCA procedure involves the insertion of an angioplasty balloon at the distal end of a catheter to the site of a stenotic lesion. Prior to treatment, the stenotic lesion is bulky and at least partially blocking the coronary artery at issue. Once advanced, the balloon is inflated compressing the stenosis and widening the lumen in order to allow an efficient flow of blood through the lumen.

Following PTCA and other stenotic treatment procedures, a significant number of patients may experience restenosis or other vascular blockage problems. These problems are prone to arise at the site of the former stenosis.

In order to help avoid restenosis and other similar problems, a stent may be implanted into the vessel at the site of the former stenosis with a stent delivery catheter. A stent is a tubular structure which is delivered to the site of the former stenosis or lesion and compressed against vessel walls thereat, again with a balloon. The structure of the stent promotes maintenance of an open vessel lumen. The stent can be implanted in conjunction with the angioplasty.

In addition to stent implantation, radiotherapy and drug delivery treatments have been developed and applied to the site of the former stenosis following angioplasty. Generally such treatments can aid in the healing process and significantly reduce the risk of restenosis and other similar problems.

In some cases, stent implantation may be combined with drug delivery or radiotherapy. For example, a stent may be drug loaded or radioactive. A stent with a therapeutic agent may be delivered to the physician about the stent delivery catheter (and with a removable shield if the stent is radioactive).

However, delivery of a therapeutic treatment throughout the site of the former stenosis is problematic. The level of uniformity in the delivery of a therapeutic agent to the injured area is dependent upon the particular stent configuration. For example, in the case a radioactive stent, the radioactive stent may have hot spots and cold spots of uneven levels of radioactivity. This is because the stent is made up of struts having radioactivity and window cells having no physical structure or radioactivity (or drug in the case of a drug delivery stent). Therefore, therapeutic agent throughout a particular stent configuration is dependent upon the strut and window cell distribution throughout that stent. Therefore, therapeutic variability results.

For example, in the case of a radioactive stent, if about 20 Grays (Gy) of radiation, as measured from 1 mm of tissue depth, are to be delivered to a vessel portion to be treated, a wide range of radiation delivery will actually occur. That is, due to the radioactive stent configuration, a non-uniform delivery, ranging from about 5 Gy to about 25 Gy is more likely delivered to the vessel portion to be treated. Due to limitations of the prior art a range of at least about 20 Gy will be delivered by a radioactive stent throughout the vessel portion to be treated in the given example. As a result, certain portions of the vessel will receive significantly more or significantly less radiation than intended. Such a variability in delivery could lead to underdose failing to reduce the risk of restenosis in certain portions of the vessel, or overdose potentially causing further vascular injury to other portions of the vessel. This variability results regardless of the therapeutic agent to be delivered.

Additionally, certain therapeutic agents are delivered to avoid a phenomenon known as "edge restenosis". Edge restenosis is prone to occur near stent ends.

Even though a stent is structurally configured to maintain the patency of a vessel lumen, edge restenosis is prone to occur with the use of radioactive stents. Edge restenosis involves the formation of vascular overgrowths in vascular areas immediately adjacent radioactive stent ends, generally within about 2 mm of each radioactive stent end. Edge restenosis is a result of delivery of a sub-threshold level of radiation to the vascular areas immediately adjacent the radioactive stent ends. These vascular areas are near or within the site of the former stenosis. They include vasculature likely to be diseased, or subjected to a recent trauma such as angioplasty. When a sub-threshold level of radiation, between about 2 Grays and about 10 Grays, as measured at 1 mm of tissue depth, reaches such vulnerable vascular areas, stenotic overgrowths may actually be stimulated. These overgrowths result in narrowed vessel portions near stent ends giving an appearance of a candy wrapper crimped around the ends of the stent. Thus, this effect is often referred to as the "candy wrapper" effect.

The occurrence of the candy wrapper effect is likely when a radioactive stent is used. This is because the intensity of radiation decreases as the source of the radiation, the radioactive stent, terminates at its ends leading to a drop of in radiation levels at vessel portions adjacent its ends. Thus, a sub-threshold radiation delivery is likely to occur near the radioactive stent ends.

As indicated, heretofore, the level of therapeutic uniformity or focus any particular stent has been able to deliver has been dependent upon that stent's configuration with respect to strut and window cell distribution. However, a stent structure (i.e. strut layout) which physically promotes maintenance of an open vessel lumen may be of a particular configuration which is not necessarily best suited for a more uniform delivery of a therapeutic agent. Additionally, this stent configuration may fail to avoid an unintended "candy wrapper" effect in which portions of the vessel adjacent the stent become narrowed.

SUMMARY OF THE INVENTION

An embodiment of the present invention provides a stent having a variable stent surface area per unit length. The variable stent surface area is used to accommodate a therapeutic agent.

Another embodiment of the present invention provides for a stent having an end and a variable stent surface area per unit length to accommodate a therapeutic agent. A decreased level of therapeutic agent in provided at the end.

An embodiment of the present invention provides for a stent having an end and a variable stent surface area per unit length to accommodate a therapeutic agent. An increased level of therapeutic agent in provided at the end.

In an embodiment of the invention a method of vessel treatment utilizing a stent with a variable stent surface area is provided. A therapeutic agent is disposed on the stent surface area to provide a patterned distribution of the therapeutic agent.

In another embodiment of the invention a method of stent manufacture is provided where indentations are cut into a surface of a stent. A therapeutic agent is disposed on the surface of the stent.

In another embodiment of the invention a method of stent manufacture is provided where struts of the stent are cut of increased thickness to provide a variable stent surface area. Therapeutic agent is disposed on the variable stent surface area.

DETAILED DESCRIPTION OF THE INVENTION

The following description makes reference to numerous specific details in order to provide a thorough understanding of the present invention. However, each and every specific detail need not be employed to practice the present invention. Additionally, well-known details, such as particular materials or methods, have not been described in order to avoid obscuring the present invention.

Figure 1:
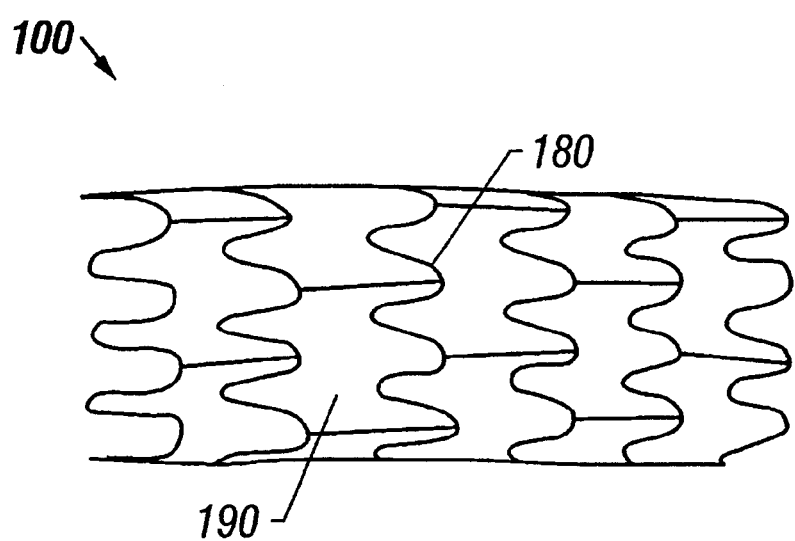
FIG. 1 is a side view of an embodiment of a stent of the present invention.

Referring to FIG. 1 an embodiment of a stent 100 of the present invention is shown. The stent 100 is formed of struts 180, which provide physical structure, and open spaces, referred to as window cells 190. The struts 180 are formed from stainless steel or other materials which are generally biocompatible. For purposes of illustration, the struts 180 shown have a cylindrical shape longitudinally. However, in alternate embodiments non-cylindrical strut 180 shapes are used. As discussed further herein the struts 180 provide a variable surface area to the stent 100.

Figure 2:
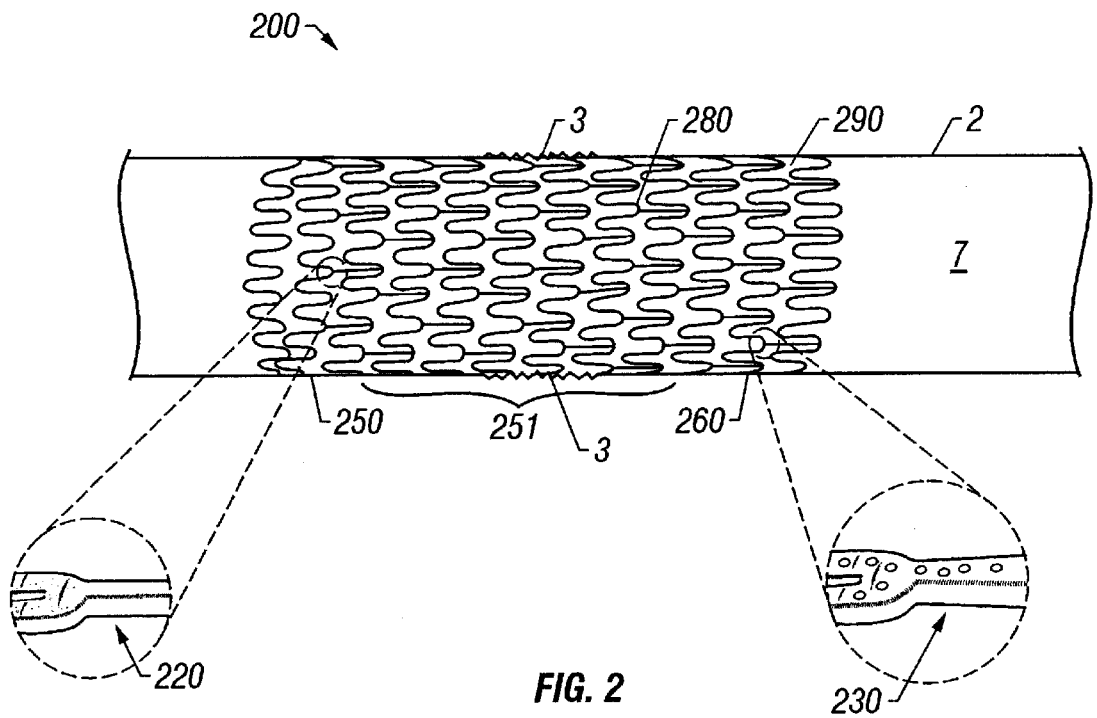
FIG. 2 is a pictorial view of an embodiment of a stent of the present invention implanted within a vessel of a patient.

Referring to FIG. 2 an embodiment of a stent 200 of the present invention is shown within a vessel 2 near the site of a former stenosis 3 to maintain the patency of the vessel lumen 7. The stent 200 of FIG. 2 is equipped with struts 280 which have variability in surface area, in terms of a change in surface area per unit length, as described further below. For each strut 280 portion, a surface area ($\gamma$) is provided which is given by the equation: $\gamma=2\pi r l h_r$, where r is a radius (r) of the strut 280 portion, l is a length (l) of the strut 280 for the portion of the strut 280 being examined, and $h_r$ is the roughness factor ($h_r$) of the strut 280 portion.

Figure 3:
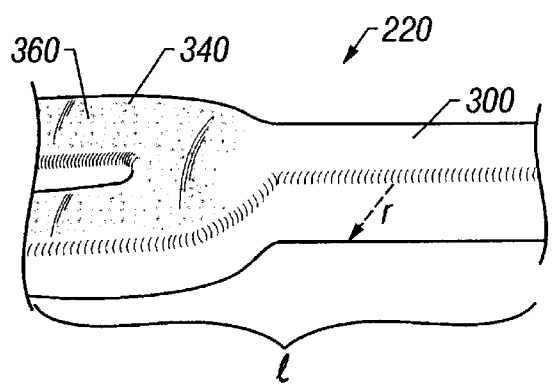
FIG. 3 is an enlarged view of an embodiment of a strut of the stent of FIG. 2.
Figure 4:
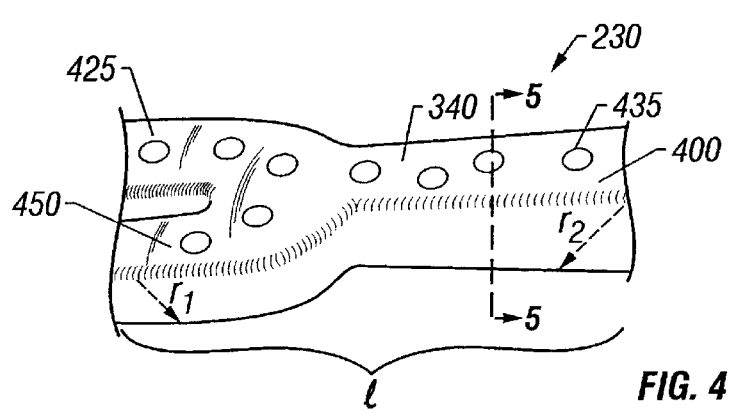
FIG. 4 is an enlarged view of an embodiment of a strut of the stent of FIG. 2.
Figure 5:
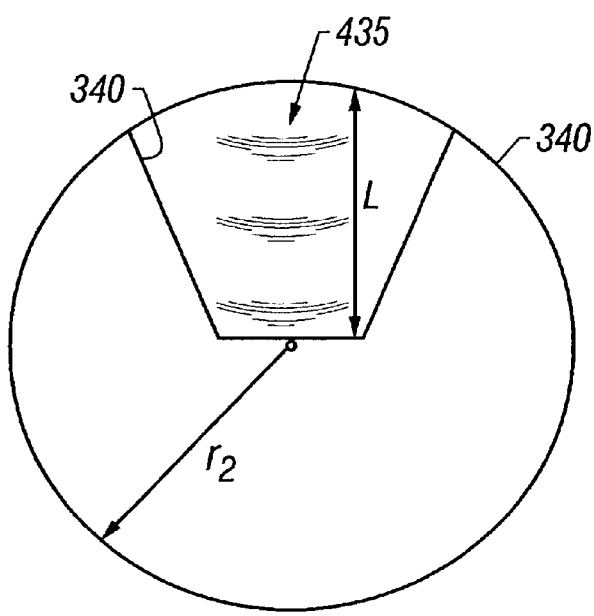
FIG. 5 is a cross sectional view of an embodiment of a strut taken along the line 5—5 of FIG. 4.

Referring to FIGS. 3 and 4, strut types 220, 230 of FIG. 2 are shown enlarged. The radius (r) (or $r_1$ and $r_2$) and a given length (l) are shown (see also FIG. 5 showing a radius ($r_2$) of a cross-section of a strut). The strut surface area ($\gamma$) includes a loading surface 340. The loading surface 340 portion of the surface area ($\gamma$) is that portion of the surface area ($\gamma$), generally facing outward (i.e. toward vessel 2 as shown in FIG. 1), that accommodates therapeutic agent. As the overall surface area ($\gamma$) increases or decreases, so does the loading surface 340. Therefore, if strut surface area ($\gamma$) varies throughout a given length (l), as it does in the embodiment shown, then the dose amount for a given length (l) (i.e. the dose concentration ($\delta$)) will vary throughout that same length (l). Given the equation: $\gamma=2\pi r l h_r$, it can be seen that if the variables r or $h_r$ of the equation fluctuate in value, for the same given length (l), as is the case in the shown embodiment, then so too will the surface area ($\gamma$) of the strut type 220, 230 within the given length (l).

Referring to FIGS. 2 and 3, in order to vary surface area ($\gamma$) of the stent 200, certain roughened strut 220 types are provided with a surface pattern. The roughened struts 220 are those in which the variable $h_r$, referred to above, has changed in value throughout a given length (l). Or, in other words, $\gamma'=2\pi r l \Delta h_r$. For example, where an entirely smooth surface strut is provided (not shown), the roughness factor ($h_r$) is 1.0, having no effect on the surface area ($\gamma$) of the smooth surface strut. However, if the roughness factor ($h_r$) is greater than 1.0, the surface area ($\gamma$) will correspondingly increase as shown in the present embodiment. Therefore, the dose concentration ($\delta$) of therapeutic agent deliverable to the vessel 2 is increased in corresponding portions of the strut 280 where ($h_r$) is greater than 1.0.

As shown in FIG. 3, an embodiment of a roughened strut 220 is provided of a given length (l). Moving from a first portion 360 of the given length (l) to a second portion 300, the roughness factor ($h_r$) changes as indicated by the change in roughness over that same length (l). That is, increased roughness, as indicated by the granular appearing texture of the loading surface 340, is provided near first portion 360. Alternatively, the value of the roughness factor ($h_r$) decreases and approaches a value of 1.0 near second portion 300 as shown by the smoother appearance of the loading surface 340 near second portion 300. Therefore, a roughened strut 220, as in the embodiment shown, provides one manner of varying surface area ($\gamma$) throughout a given length (l), and thus provides a variation in dose concentration ($\delta$) throughout that same length (l).

Referring to FIGS. 2 and 3, in order to increase the roughness factor ($h_r$) chemical, plasma, laser, mechanical or alternate methods of etching are used in embodiments of the invention. For example, in one embodiment the stent 200 is dry etched by sand blasting or plasma etched with argon in order to increase roughness.

Another embodiment focuses the increased roughness factor ($h_r$) at particular struts 280 by a lithography technique of coating the stent 200 with a protective polymer such as ethylene vinyl alcohol. The stent 200 is then selectively treated with a solvent, such as dimethyl sulfoxide (DMSO), dimethyl formamide (DMF), or dimethyl acetamide (DMAc), in strut 280 areas to remove portions of the protective polymer. For example, in one embodiment, a stent end 250 is dipped into the solvent to remove protective polymer from portions of the struts 280 nearer the stent end 250. By removing the protective polymer, these portions of the stent 200 are susceptible to increased roughening following application of an etching process to an exterior of the stent. Thus, once the stent 200 is etched, an increased roughness factor ($h_r$) is present at the stent end 250. However, in an alternate embodiment increasing roughness interior of the stent 1 is avoided in order to promote a flow of blood through the stent.

The roughened strut 220 embodiment shown is viewed in light of its positioning in the stent 200. It can be seen that the roughened strut 220 is found near stent end 250. The roughened strut 220 includes a loading surface 340 which has been roughened as discussed above. The degree of roughening increases moving toward the first portion 360 (nearer the stent end 250) of the roughened strut 220. Alternatively, the loading surface 340 becomes smoother moving toward a second portion 300 (nearer the stent body 251). That is, in view of the stent 200 as a whole, additional surface area ($\gamma$), and thus, increased radioactivity upon activation, is found near the stent end 250 due to the roughened strut 220 patterning provided.

Referring to FIGS. 2 and 4, in order to vary surface area ($\gamma$) of the stent 200, certain struts 280 are formed as increased thickness struts 230. The increased thickness struts 230 are those in which the radius (r), referred to above, has changed in value throughout a given length (l). Or, in other words, $\gamma'' = 2\pi \Delta r l h_r$.

As shown in FIG. 4, an embodiment of an increased thickness strut 230 is provided of a given length (l). Moving from a first strut portion 450 of the given length (l) to a second strut portion 400, we see that the radius ($\Delta r$) changes as indicated by the change in radius size from $r_1$ to $r_2$ respectively, with $r_2$ indicating an increased radius (i.e. $\Delta r$) from that of $r_1$. Therefore, an increased thickness strut 230 provides an alternate manner of varying surface area ($\gamma$) throughout a given length (l), and thus allowing for a variable dose concentration ($\delta$) throughout that same length (l). This pattern of surface area ($\gamma$) along the given length (l) holds true even in non-linear strut portions 425.

As shown with reference to positioning within the stent 200, the increased thickness strut 230 is shown near opposite stent end 260 of FIG. 1. As a result, increased surface area ($\gamma$) and thus, increased radioactivity upon activation, is provided near opposite stent end 260.

In a method of manufacturing the stent 200, including struts 280, the stent 200 is laser cut from, for example, a stainless steel tube. The laser cutting process is run according to an automated process to form a particular stent configuration. In order to increase or vary a radius (r) in portions of particular struts 280, the automated process is programmed to cut a strut 280 of increasing radius (r), for example, near opposite stent end 260. In this manner, an increased thickness strut 230 is provided.

Referring to FIGS. 4 and 5, a cross section taken from the line 5—5 of FIG. 4 is shown as FIG. 5. In addition to a greater amount of loading surface 340 generally, the increased thickness strut 230 of FIG. 4 includes increased size indentations 435. As shown in the embodiment of FIG. 5, the increased size indentations 435 have been cut into the loading surface 340 with a laser during manufacture to provide additional loading surface 340 at the interior of the increased size indentations 435 by providing additional interior surface with the increased size indentations 435.

Each indentation may increase surface area by about threefold per unit area. Where the depth L is increased, surface area provided by the indentation is increased. Increased size indentations may have a depth L of about one half of the increased thickness strut 230 at the location of the indentation. Increased size indentations 435, have a depth L beyond about 60–80 microns, and are provided as thickness increases (as shown toward the opposite strut end 400 of FIG. 4). The increased size indentations 435 provide a volume as well as increased surface area ($\gamma$). In the embodiment shown, the indentations 435 are of a truncated cone shape. However, in other embodiments, other shapes are used. For example, in one embodiment of the invention, the indentations 435 are of a dimpled shape Referring to all of FIGS. 2–5, the surface area ($\gamma$) discussed in relation to the above embodiments is increased by the use of particular increased size indentations 435, an increased thickness strut 230, and a roughened strut 220. However, all of these features, alone and in any combination, are used in other embodiments to increase surface area ($\gamma$) in particular stent 200 portions and provide particularly configured and focused loading surfaces 340 for accommodating therapeutic agents. Once a particular stent 200 configuration of increased surface area ($\gamma$) is chosen and provided, it is activated with therapeutic agent, accommodated at the loading surface 340.

In an embodiment of the invention, where the therapeutic agent to be provided includes radioactive isotopes, plasma ion implantation of the isotopes into the loading surface 340 is used for activation. Embodiments of the invention employ Plasma and Ion Beam Assisted Deposition for loading. Plasma ion implantation results in radioactive ions being implanted below the loading surface 340 of the stent 200. By implanting ions below the loading surface 340, a radioactive layer is formed which is shielded from a biological environment when the stent 200 is later inserted into a patient. Plasma ion implantation involves loading the stent 200 into an isolation chamber where a plasma of radioactive ions is generated. The plasma is provided by providing a liquid or gas which includes a stable precursor to the ion type to be used. Radio Frequency (RF) or microwave power are coupled to the isolation chamber to transform the mixture into a plasma state within the chamber. Negative voltage energy pulses are then applied to the treatment stent 1 to cause implantation of ions below the loading surface 40. In various embodiments, ions such as Phosphorous ($p^{32}$), Rhenium ($Re^{188}$), Yttrium ($Y^{90}$), Palladium ($Pd^{103}$), Iodine ($I_{125}$), and Ruthenium ($Ru^{106}$) are loaded above and below the loading surface 340 in this manner.

In other embodiments, where the therapeutic agent to be provided includes bioactive drugs, alternate methods of loading onto the loading surface 340 are used. For example, a dip coating, spray, or centrifugation process is used. The dip coating process involves submerging the stent 200 in a solvent having an anti-coagulant or other drug solution. Heparin or heparin coating substances such as Duraflo®, available from Baxter International, Inc., are used as part of the drug solution.

The stent 200 is then placed into a centrifugation chamber and spun to direct the first solution to particular portions of the stent 200. The stent 200 is then dried and submerged in a second drug solution. This second drug solution also contains radioactive ions as additional therapeutic agent.

Mechanical rinsing of the stent 200 is used to remove any excess of the drug solution. Centrifugation of the stent 200 is then repeated to remove excess drug solution.

In one embodiment, where a volume is provided by increased size indentations 435, drug solution is deposited therein as a result of such methods of loading described above. In other embodiments, such methods of loading are repeated to add bioactive elutable drugs or even a separate anti-coagulant barrier to encase drug solution on the loading surface 340. The barrier is added by dipping, centrifugation and plasma deposition as indicated, or alternately by spraying or plasma polymerization.

The variability in surface area provided by any combination of the above referenced features accommodating a therapeutic agent allows delivery of therapeutic agent in a manner not limited solely to strut 280 and window cell 290 distribution. As a result, stent 200 embodiments are provided which increase therapeutic agent focus in particular areas of the stent 200.

In an embodiment of the invention, increased surface area is provided in areas of the stent 200 known to deliver an under-dose of therapeutic agent. Alternatively in another embodiment, less surface area is present in areas known to deliver an overdose of therapeutic agent. These surface area configurations are used to help avoid irregularities or significant variation in delivery of therapeutic agent.

Additionally, in an embodiment of the invention, increased surface area struts 280 are developed to focus an increased amount of therapeutic agent near stent ends 250, 260. This embodiment helps avoid delivery of sub-threshold levels of radiation to portions of a vessel immediately adjacent stent ends 250, 260 (i.e. to avoid delivery of between about 2 and about 10 Grays, as measured at 1 mm of tissue depth to the vessel 2 in this area). Likewise, another similar embodiment helps provide other therapeutic agents to help combat edge restenosis in this manner. Alternatively, variability in surface area can be used to minimize delivery of a radioactive therapeutic agent near stent ends 250, 260 in order to avoid sub-threshold radiation delivery and edge restenosis.

FIGS. 6–9 show the results of making use of particular variable surface area stent embodiments having unique focuses of therapeutic agent distribution. The results are shown with respect to dose delivery and source profiles.

Figure 6:
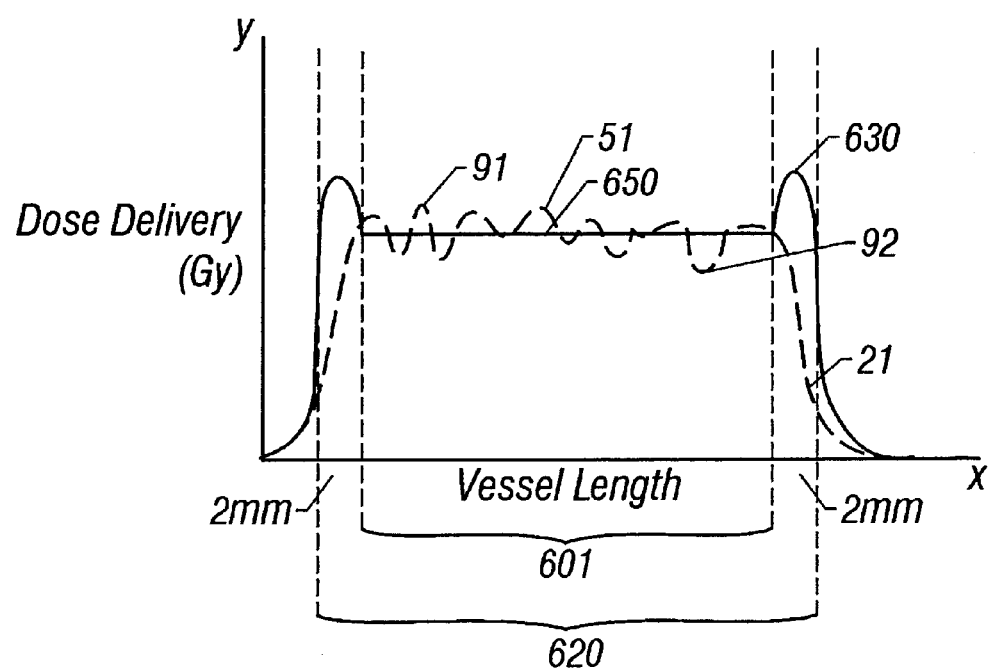
FIG. 6 is a chart depicting an embodiment of a dose delivery profile of the present invention.

For example, FIG. 6 depicts a chart indicating the distribution of therapeutic agent, in the form of radioisotopes, with respect to dose delivery for an embodiment of the invention. The x-axis, labeled "Vessel Length", includes the stent length 601 along with the treatment portion 620 of a vessel. The y-axis, labeled "Dose Delivery (Gy)", indicates the amount of radiation absorbed in Grays (Gy) throughout a vessel 2 such as that of FIG. 1 (as measured from 1 mm of vessel depth).

Figure 7:
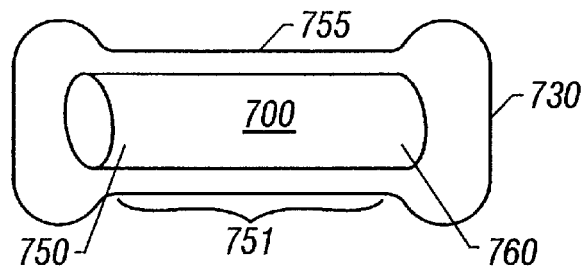
FIG. 7 is a representation of an embodiment of a source profile of the invention.

Similarly, FIG. 7 represents a source profile of a stent 700 according to the therapeutic distribution indicated in the embodiment of FIG. 6. The profile includes an extension of radioactivity 730 significantly beyond stent ends 750, 760 (i.e. hot ends) to help avoid edge restenosis. Also, a uniform field of radioactivity 755 throughout the stent body 751 is provided.

With reference to the embodiments represented in FIGS. 6 and 7, an increased amount of therapeutic agent is provided near stent ends 750, 760 due to the increased loading surface provided thereat. Therefore, where the therapeutic agent is radiation, as with the embodiments of FIGS. 6 and 7, delivery of a sub-threshold level of radiation is avoided at vessel portions immediately adjacent the stent 700 (i.e. within about 2 mm of the stent longitudinally).

Additionally, the stent 700 is configured with increased loading surface directed toward portions of the stent 700 previously responsible for a more uneven distribution of therapeutic agent. In the case of radiation delivery, a more uniform field of radioactivity 755 provides a more consistent delivery of therapeutic agent (i.e. radiation) throughout the stent body 751 of the stent 700.

A prior art distribution of radiation 51 is un-even. That is, the uniform surface area of a prior art stent may deliver a highly variable dose within a stent length 601. For example, the variable dose can include a maximum dose 91 that is 20 Gy greater than a minimum dose 92 while delivering only an average dose of 20 Gy (with all measurements taken at 1 mm of tissue depth). Alternatively, a more level delivery of radioactivity 650 is provided in embodiments of the invention. Embodiments of the invention can also include peak deliveries of radioactivity 630 to ensure avoidance of sub-threshold delivery 21 in vessel areas of concern, within about 2 mm of the stent longitudinally.

Figure 8:
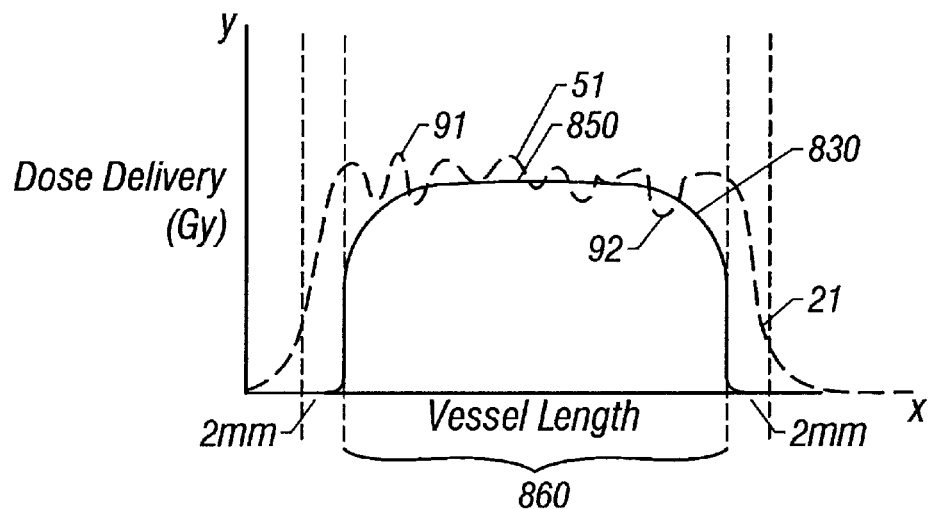
FIG. 8 is a chart depicting an embodiment of a dose delivery profile of the present invention.
Figure 9:
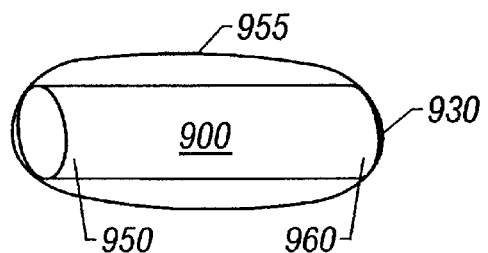
FIG. 9 is a representation of an embodiment of a source profile of the invention.

Referring to FIGS. 8 and 9, and continuing with the example of a radioactive therapeutic agent, a decreased amount of radioactivity (i.e. an early termination of radioactivity 930) is provided near stent ends in another embodiment of the invention. This is due to the decreased loading surface provided at the stent ends 950, 960 as compared to the remainder of the stent 900. Delivery of a sub-threshold level of radiation is nevertheless minimized or avoided at portions of a vessel immediately adjacent the stent 900 (i.e. within about 2 mm of the stent ends 950, 960). That is, any radiation delivered here is below a sub-threshold level to help avoid edge restenosis.

Additionally, as with FIG. 6, the stent 900 represented by FIG. 9 has been configured to have increased surface area directed toward portions of a stent 900 that would otherwise be responsible for an uneven distribution of therapeutic agent. A more uniform field of radioactivity 955 provides a more consistent delivery of therapeutic agent (i.e. radiation) throughout a stent body of the stent 900 as seen above the x-axis throughout stent length 860.

Again, by way of comparison, a prior art distribution of radiation 51 is uneven and a sub-threshold level of radiation 21 is delivered by a prior art stent to vessel areas within 2 mm of the stent. Alternatively, a more level delivery of radioactivity 850 is provided in embodiments of the invention. Embodiments of the invention can also include tapered deliveries of radioactivity 830 to ensure avoidance of sub-threshold delivery 21 in vessel areas of concern.

Embodiments of the invention described above include a therapeutic stent which is able to provide an overall pattern of therapeutic agent, where the pattern is not determined solely by strut and window cell distribution throughout the stent. Embodiments of the invention also include patterns of therapeutic agent which help avoid edge restenosis while also helping to avoid delivery of a non-uniform level of therapeutic agent throughout the portion of a vessel to be treated. While such exemplary embodiments have been shown and described in the form of particular stents having variable surface area, many changes, modifications, and substitutions may be made without departing from the spirit and scope of this invention.

We claim:

1. A drug eluting stent, comprising:
   a body having a first end and a second end and a middle segment between said first and second ends;
   a variable stent surface area per unit length of said body, wherein said first and second ends have a lesser surface area than said middle segment; and
   a drug deposited on said stent so that said first and second ends have a lesser amount of said drug than said middle segment.

2. The stent of claim 1, wherein said body comprises struts having a roughened portion with a roughness factor above 1 to provide said variable stent surface area.

3. The stent of claim 2, wherein said roughened portion is provided by a method of etching a portion of said struts.

4. The stent of claim 2, wherein said struts comprise:
- a loading surface at an exterior portion of said stent to accommodate said drug; and
- an interior portion of said stent void of said roughened portion.

5. The stent of claim 1, wherein said body comprises struts having a thickened portion to provide said variable stent surface area.

6. The stent of claim 5, wherein said thickened portion is provided by an increased radius portion.

7. The stent of claim 5, wherein said thickened portion is provided by cutting a stent pattern from a tube, said stent pattern indicating said thickened portion.

8. The stent of claim 7, wherein said cutting is performed by an automated laser method.

9. The stent of claim 1, wherein said body comprises increased size indentations having a depth beyond about 80 micrometers to provide said variable stent surface area.

10. The stent of claim 1, wherein said drug is deposited in a polymeric coating.

11. The stent of claim 1, wherein said drug is an anti-coagulant.

12. The stent of claim 1, wherein said drug is encased in an anti-coagulant barrier.

13. A drug eluting stent, comprising:
- a body having a first end and a second end and a middle segment between said first and second ends;
- a variable stent surface area per unit length of said body, wherein said first and second ends have a greater surface area than said middle segment; and
- a drug deposited on said stent so that said first and second ends have a greater amount of said drug than said middle segment.

14. The stent of claim 13, wherein said body comprises struts having a roughened portion with a roughness factor above 1 to provide said variable stent surface area.

15. The stent of claim 14, wherein said roughened portion is provided by a method of etching a portion of said struts.

16. The stent of claim 13, wherein said struts comprise:
- a loading surface at an exterior portion of said stent to accommodate said drug; and
- an interior portion of said stent void of said roughened portion.

17. The stent of claim 13, wherein said body comprises struts having a thickened portion to provide said variable stent surface area.

18. The stent of claim 17, wherein said thickened portion is provided by an increased radius portion.

19. The stent of claim 17, wherein said thickened portion is provided by cutting a stent pattern from a tube, said stent pattern indicating said thickened portion.

20. The stent of claim 19, wherein said cutting is performed by an automated laser method.

21. The stent of claim 13, wherein said body comprises increased size indentations having a depth beyond about 80 micrometers to provide said variable stent surface area.

22. The stent of claim 13, wherein said drug is deposited in a polymeric coating.

23. The stent of claim 13, wherein said drug is an anti-coagulant.

24. The stent of claim 13, wherein said drug is encased in an anti-coagulant barrier.

25. A drug eluting stent, comprising:
- a stent body having a first end, an opposing second end, and a middle segment positioned between said first and second ends; and
- a drug disposed on said stent, wherein the concentration or amount of said drug is higher at said first or second end as compared to said middle segment of said body positioned between said first and second ends.

26. The stent of claim 25, wherein said stent is used to deliver said drug for the treatment of edge-restenosis.

27. The stent of claim 25, wherein said drug is released from a polymer.

28. The stent of claim 25, wherein the concentration or amount of drug is higher at both said first and second ends as compared to said middle segment.

29. The stent of claim 25, wherein said body is made from a plurality of interconnected struts such that the surface area of at least some of the individual struts forming said first or second end is greater than the surface area of said struts forming said middle segment of said body so that a higher concentration or amount of said drug can be carried by said having a greater surface area.

\* \* \* \* \*

UNITED STATES PATENT AND TRADEMARK OFFICE
CERTIFICATE OF CORRECTION

PATENT NO. : 6,764,505 B1  
DATED : July 20, 2004  
INVENTOR(S) : Hossainy et al.

Page 1 of 1

It is certified that error appears in the above-identified patent and that said Letters Patent is hereby corrected as shown below:

<u>Title page,</u>  
Item [56], References Cited, OTHER PUBILCATIONS, change "U.S. patent application Ser. No. 09/697,103, Hossainy et al., filed Oct. 26, 2000" to -- U.S. patent application Ser. No. 09/697,106, Hossainy et al., filed Oct. 26, 2000. --

Signed and Sealed this

Eleventh Day of January, 2005

JON W. DUDAS  
*Director of the United States Patent and Trademark Office*

UNITED STATES PATENT AND TRADEMARK OFFICE
CERTIFICATE OF CORRECTION

PATENT NO. : 6,764,505 B1  Page 1 of 1
APPLICATION NO. : 09/834012
DATED : July 20, 2004
INVENTOR(S) : Syed F.A. Hossainy et al.

It is certified that error appears in the above-identified patent and that said Letters Patent is hereby corrected as shown below:

Title page, item [75] inventors: add -- Orlando Padilla --

Signed and Sealed this

Fifth Day of December, 2006

JON W. DUDAS
*Director of the United States Patent and Trademark Office*